US010016811B2

(12) United States Patent
Neal

(10) Patent No.: US 10,016,811 B2
(45) Date of Patent: Jul. 10, 2018

(54) ORTHOPEDIC IMPLANTS AND METHODS OF MANUFACTURING ORTHOPEDIC IMPLANTS

(71) Applicant: David J. Neal, Morris Plains, NJ (US)

(72) Inventor: David J. Neal, Morris Plains, NJ (US)

(*) Notice: Subject to any disclaimer, the term of this patent is extended or adjusted under 35 U.S.C. 154(b) by 422 days.

(21) Appl. No.: 14/455,524

(22) Filed: Aug. 8, 2014

(65) Prior Publication Data

US 2015/0045903 A1    Feb. 12, 2015

Related U.S. Application Data

(60) Provisional application No. 61/864,091, filed on Aug. 9, 2013.

(51) Int. Cl.

| B22F 3/105 | (2006.01) |
|---|---|
| B22F 7/00 | (2006.01) |
| B23K 15/00 | (2006.01) |
| B23K 26/00 | (2014.01) |
| B23K 26/32 | (2014.01) |
| B23K 26/342 | (2014.01) |
| B22F 5/10 | (2006.01) |
| B22F 7/06 | (2006.01) |
| A61F 2/42 | (2006.01) |
| A61F 2/30 | (2006.01) |

(Continued)

(52) U.S. Cl.
CPC ............ *B22F 7/004* (2013.01); *B22F 3/1055* (2013.01); *B22F 5/106* (2013.01); *B22F 7/06* (2013.01); *B23K 15/0006* (2013.01); *B23K 15/0086* (2013.01); *B23K 26/0006* (2013.01); *B23K 26/0081* (2013.01); *B23K 26/32* (2013.01); *B23K 26/342* (2015.10); *A61F 2/3094* (2013.01); *A61F 2002/30011* (2013.01); *A61F 2002/3097* (2013.01); *A61F 2002/30118* (2013.01); *A61F 2002/30131* (2013.01); *A61F 2002/30133* (2013.01); *A61F 2002/30153* (2013.01); *A61F 2002/30156* (2013.01); *A61F 2002/30158* (2013.01); *A61F 2002/30187* (2013.01); *A61F 2002/30224* (2013.01); *A61F 2002/30962* (2013.01); *A61F 2002/4207* (2013.01); *A61F 2002/4223* (2013.01); *A61F 2310/00011* (2013.01); *B23K 2203/05* (2015.10); *B23K 2203/08* (2013.01); *B23K 2203/14* (2013.01); *B23K 2203/15* (2015.10); *B23K 2203/26* (2015.10); *B23K 2203/50* (2015.10); *Y02P 10/295* (2015.11)

(58) Field of Classification Search
CPC .................................................. B22F 3/1055
See application file for complete search history.

(56) References Cited

U.S. PATENT DOCUMENTS

| 4,863,538 A | 9/1989 | Deckard |
|---|---|---|
| 4,944,817 A | 7/1990 | Bourell et al. |

(Continued)

*Primary Examiner* — Jessee R Roe
*Assistant Examiner* — Ngoclan T Mai
(74) *Attorney, Agent, or Firm* — Kim Winston LLP

(57) ABSTRACT

A method of manufacturing an orthopedic implant is provided. The method includes creating a 3D model of an orthopedic implant having a solid portion and a porous portion and selectively adjusting a physical property of at least one of porosity of the porous portion, lattice thickness of the porous portion, beam profile of the porous portion, and topography of the 3D model. The entire implant is then additively manufactured based on the 3D model.

14 Claims, 20 Drawing Sheets

(51) Int. Cl.
*B23K 103/08* (2006.01)
*B23K 103/00* (2006.01)
*B23K 103/14* (2006.01)
*B23K 103/04* (2006.01)
*B23K 103/18* (2006.01)

(56) References Cited

U.S. PATENT DOCUMENTS

| | | | |
|---|---|---|---|
| 5,017,753 A | 5/1991 | Deckard | |
| 5,076,869 A | 12/1991 | Bourell et al. | |
| 7,537,664 B2 * | 5/2009 | O'Neill | A61F 2/30907 |
| | | | 148/513 |
| 8,532,806 B1 | 9/2013 | Masson | |
| 8,545,572 B2 | 10/2013 | Olson | |
| 8,728,387 B2 * | 5/2014 | Jones | A61F 2/30907 |
| | | | 148/525 |
| 8,735,773 B2 | 5/2014 | Lang | |
| 8,843,229 B2 * | 9/2014 | Vanasse | A61F 2/28 |
| | | | 600/421 |
| 2006/0147332 A1 * | 7/2006 | Jones | B22F 3/1055 |
| | | | 419/8 |
| 2013/0199748 A1 * | 8/2013 | Christensen | B22F 3/1055 |
| | | | 164/494 |

* cited by examiner

ORTHOPEDIC IMPLANTS AND METHODS OF MANUFACTURING ORTHOPEDIC IMPLANTS

CROSS-REFERENCE TO RELATED APPLICATIONS

This application claims the benefit of U.S. Provisional Application No. 61/964,091, filed Aug. 9, 2013, the entire disclosure of which is incorporated by reference herein in its entirety.

BACKGROUND OF THE INVENTION

The present invention relates generally to orthopedic implants and methods of manufacturing an orthopedic implant. In particular, the present invention relates to an orthopedic implant having a porous portion and a solid portion manufactured by an additive manufacturing process.

In the realm of orthopedic surgery, it is known to use implants to fix the position of bones. In this way, bones can be reconstructed, and malformations or other injuries corrected. However, different bones within the body have different functions and as such are exposed to different forces and stresses. Consequently, a single type of orthopedic implant is not well suited for implantation into the various types of bones which experience different forces and stresses.

Thus, the foregoing deficiencies of conventional implants can be overcome by engendering a method of manufacturing an orthopedic implant capable of selectively adjusting a physical property of the implant to account for the differing types of forces and stresses the implant is expected to be exposed to. This is accomplished by the orthopedic implants and methods of manufacturing the implants of the present invention.

BRIEF SUMMARY OF THE INVENTION

In accordance with a preferred embodiment, the present invention provides a method of manufacturing an orthopedic implant comprising the steps of creating a 3D model of a part having a solid portion and a porous portion, selectively adjusting a physical property of at least one of porosity of the porous portion, lattice thickness of the porous portion, beam profile of the porous portion, and topography of the 3D model, and additively manufacturing the entire part based on the 3D model.

In accordance with another preferred embodiment, the present invention provides an orthopedic implant comprising a solid portion and a porous portion each formed by additive manufacturing the entire implant based on a 3D model of the implant having a physical property selectively adjusted based upon a position the implant is to be implanted in bone.

In accordance with yet another preferred embodiment, the present invention provides an orthopedic implant comprising a first solid portion, a second solid portion, a first porous portion, and a second porous portion. The second solid portion is spaced from and circumscribes the first solid portion. The first porous portion is between the first and second solid portions. The second porous portion circumscribes the second solid portion. The implant is formed completely by additive manufacturing based on a 3D model of the implant. A surface area percentage of at least one of the first solid portion, second solid portion, first porous portion, and second porous portion is modified based upon a position the implant is to be implanted in bone.

In accordance with another preferred embodiment, the present invention provides various embodiments of a foot and ankle porous orthopaedic implant device utilizing specialized CAD software to selectively adjust and optimize properties of porous and solid structures and fabricated using e.g., Direct Metal Laser Sintering (DMLS) or Electron Beam Melting (EBM) method using a variety of materials including, but not limited to, titanium (CP and alloy), cobalt chrome, stainless steel, magnesium, niobium, and tantalum. These devices are used for correcting various foot and ankle deformities, disorders, and trauma for both adult as well as pediatric patients. Where applicable, the devices are anatomically shaped and sized, in part, based on sawbone models (such as that available from Pacific Research). A porous band is provided around the periphery of the implants to promote involucrum. Solid portion(s) are provided for strength of clinical loading patterns. Holed and non-holed implant design options are available. The holed option provides for a variety of biologics (ie: allograft, autograft, etc) and/or ancillary fixation (screws, pins, etc). Various angle wedges, multiple thickness blocks, and several rod diameters are provided to meet the clinical needs. The advantages of these devices over the traditional bone sources (allograft, autograft) for correction include, but are not limited to: Pre-sized for optimal fit, Reliable and consistent strength, and Increased safety/lower risk of infection.

Various embodiments of these foot and ankle designs include, but are not limited to: 1st metatarsal wedge, MTP (1st metatarsal/phalange) block, TMT (Lapidus) (1st metatarsal/cuneiform) block, Calcaneal-cuboid block, Medial cuneiform opening wedge, Calcaneal lengthening/angle correcting wedge, Navicular-cuneiform block, Talar-navicular block, Ankle (tibial/talar) block, Ankle subtalar (talar/calcaneous) block, Ankle (tibial/talar/calcaneous) rod, Femur and tibial osteotomy opening wedge, and Talar/navicular/cuneiform rod. Additionally, a variety of fixation plates (straight, H, T, Y, etc), staples and screws (3.5, 4.5, 5.5 mm, etc) may be manufactured using the DMLS or EBM process.

The designs utilize a commercially available CAD software program (such as that provided by Within Medical) to model the porous structures. The advantage of utilizing this CAD software program is the ability to selectively adjust and optimize properties (ie: pore size of lattice-density, lattice thickness, beam profile, topology, etc). By selectively adjusting and optimizing the properties, the implants can be designed to withstand physiological loads especially at stress intensive areas (ie: around holes; load bearing locations, and other stress inducing features). A minimum pore diameter in a range of 200 µm to 500 µm is used to promote bone ingrowth. A pore diameter of 200 µm corresponds to the average diameter of an osteon in human bone, while a pore diameter of 500 µm corresponds to remodeled cancellous bone.

To take advantage of these selectively adjusted and optimized porous properties provided by the CAD software, the preferred commercially available manufacturing method is to utilize Direct Metal Laser Sintering, or DMLS, as it has been optimized for this computer program. DMLS allows the device to be fabricated in such a manner as to alternate from a porous structure to a solid structure as it is built layer by layer. One such manufacturing system that is compatible with the described CAD software is provided by Electro Optical Systems (EOS). Additionally, EBM is an alternate manufacturing method provided by Arcam. Another advantage of using this system is the cost savings over specialized and conventional manufacturing methods, as it is less affected by set-up costs, economies of scale, and requires minimal steps to fabricate the device.

The implant materials utilize a variety of DMLS or EBM powders that could be used for medical use (titanium, cobalt chrome, stainless steel, magnesium, niobium, tantalum, etc). Such DMLS or EBM powders may include those provided by Electro Optical Systems and Arcam.

Where applicable, the devices utilize general surgical instrumentation readily available in an orthopaedic operating room. Where applicable however, provisionals (trial devices) and other device specific surgical instruments can be provided as a single-use, sterile kit to minimize the risk of infection from improper sterilization of reusable instrumentation. Furthermore, these instruments can also be manufactured in a rapid prototyping fashion. Also, these kits will provide for a quicker operating room turnover time, as the surgical tools do not have to be cleaned and re-sterilized.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Reference will now be made in detail to the preferred embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, front, rear, side, above, below and diagonal, are used with respect to the accompanying drawings. Such directional terms used in conjunction with the following description of the drawings should not be construed to limit the scope of the invention in any manner not explicitly set forth. Additionally, the term "a," as used in the specification, means "at least one." The terminology includes the words above specifically mentioned, derivatives thereof, and words of similar import.

Figure 1:
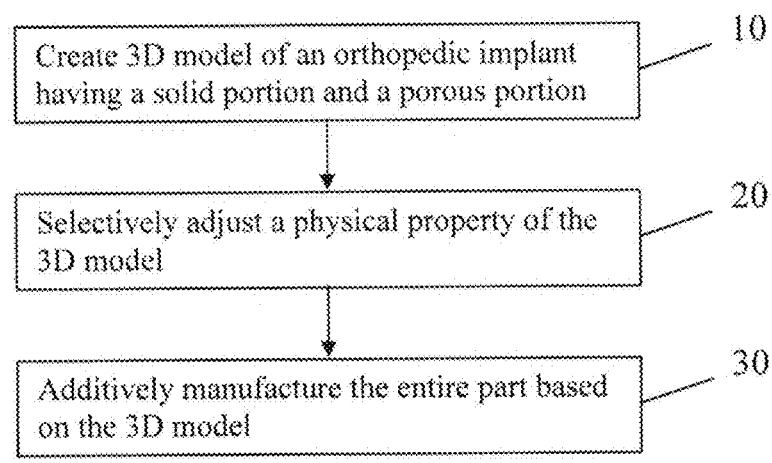
FIG. 1 is a flow diagram of a preferred embodiment of a method of manufacturing an implant in accordance with the present invention.

Referring to FIG. 1, there is shown a flow diagram of a preferred embodiment of a method of manufacturing an orthopedic implant. The method includes creating a 3D model of a part, i.e., an orthopedic implant, having a solid portion and a porous portion 10, selectively adjusting a physical property of at least one of porosity of the porous portion, lattice thickness of the porous portion, beam profile of the porous portion, and topography of the 3D model 20, and additively manufacturing the entire part based on the 3D model 30. As such, the entire orthopedic implant is formed as a unitary part, including the solid and porous portions.

The 3D model can be manufactured using commercially available systems and software, e.g., software by Within Medical of London, United Kingdom. The 3D model is a computer generated three-dimensional model or simulation of the implant. Such 3D models are known in the art and a detailed description of them is not necessary for a complete understanding of the present invention.

The orthopedic implant can be, for example, a wedge implant (e.g., a metatarsal wedge or block), a talar-navicular implant, an ankle block, an ankle rod implant, an ankle subtalar block, or a talar navicular cuneiform rod. The wedge implant can be configured to have a cross-sectional profile that is D-shaped, donut-shaped, teardrop-shaped, triangular shaped, rectangular shaped, frustum-shaped, trapezoidal shaped, or sickle-shaped.

In selectively adjusting the physical property of the 3D model of the orthopedic implant, at least one of porosity of the porous portion, lattice thickness of the porous portion, beam profile of the porous portion, and topography is adjusted. While the foregoing physical properties are preferred for selective adjustment, other physical properties inclusive of intensive and extensive properties can be additionally adjusted for example, but not limited to, density, ductility, electrical conductivity, hardness, malleability, permeability, strength, and stiffness. Additionally, material properties in addition to physical properties can be selectively adjusted. The physical properties of the 3D model are selectively adjusted based upon a determined implantation position of the implant in bone. For example, the physical properties of the 3D model are modified or varied based on whether the implant is determined to be implanted into a talar bone, a calcaneus bone, a tibia bone, a femur bone, etc. By selectively adjusting and optimizing the physical properties of the 3D model of the orthopedic implant, the implant can be designed to better withstand physiological loads, especially at stress intensive areas e.g., near fixation holes, load bearing locations, and other stress inducing features.

In other words, the physical properties of the orthopedic implant 3D model and consequently the orthopedic model are selectively adjusted or modified based upon the intended use of the implant. That is, the physical property is selectively adjusted based upon the type of bone and location within the bone the implant is to be implanted. For example, an implant configured as a calcaneal-cuboid block will be exposed to relatively high impact and shear stresses, thus the calcaneal-cuboid block can be selectively adjusted to have a higher percentage of its surface area formed by the solid portion and its topography adjusted to include an aperture for inclusion of a fastener e.g., a screw or pin. Alternatively, the calcaneal-cuboid block can be selectively adjusted to have its beam profile of its pores portion to be as thick as possible to accommodate high stresses. In another example of an osteotomy wedge, the implant can be selectively adjusted to have a higher percentage of its surface area formed by the porous portion having a high porosity and greater lattice thickness so as to promote bone ingrowth into the implant.

The orthopedic implant is manufactured by additively manufacturing the entire part, inclusive of the porous portion and the solid portion, based on the 3D model of the part with its physical properties selectively adjusted. The part can be manufactured by any additive manufacturing process but is preferably manufactured using direct metal laser sintering (DMLS) the entire part or by selective laser sintering the entire part. An example of direct metal laser sintering process applicable to the present invention is practiced by EOS of Novi, Mich. An example of selective laser sintering applicable to the present invention is disclosed in U.S. Pat. Nos. 4,863,538; 5,017,753; 5,076,869 and 4,944,817, the entire disclosures of which are hereby incorporated by reference in their entirety.

Preferably, the porous portion of the implant is configured with a minimum pore diameter ranging from about 200 µm to 500 µm for promoting bone ingrowth.

The advantages of additively manufacturing the entire part include single unit operation fabrication for manufacturing complete parts of various configuration having both a porous portion and a solid portion, and which are capable of manufacturing complex porous structures with the ability to adjust porosity, lattice thickness and beam profile of the porous structure. Another advantage of additive manufacturing the orthopedic implant is reduced manufacturing costs compared to specialized and conventional manufacturing methods. This results from lower set up costs and economies of scale associated with additive manufacturing one-off components. This is especially beneficial if the implant is a custom implant for a specific patient, in which conventional manufacturing processes would not be easily able to accommodate.

The materials applicable to manufacturing the orthopedic implant include, but are not limited to, titanium, cobalt chrome, stainless steel, magnesium, niobium, tantalum, etc.

In accordance with another preferred embodiment, the present invention provides an orthopedic implant 100 that includes a solid portion and a porous portion each formed by additive manufacturing the entire implant in a single unit operation based on a 3D model of the implant having a physical property selectively adjusted based upon a determined position the implant is to be implanted in bone. Thus, the orthopedic implant is of unitary construction. In other words, the solid and porous portions are formed as a single unitary part. The physical property is at least one of porosity of the porous portion, lattice thickness of the porous portion, beam profile of the porous portion, and topography. The orthopedic implant 100 can be configured, for example, as a wedge implant, a talar navicular implant, an ankle block, an ankle subtalar block, an ankle rod or a talar navicular cuneiform rod. Further, the wedge implant can be configured to have a sloped configuration or a non-sloped configuration, e.g., a spacer block.

Figure 2:
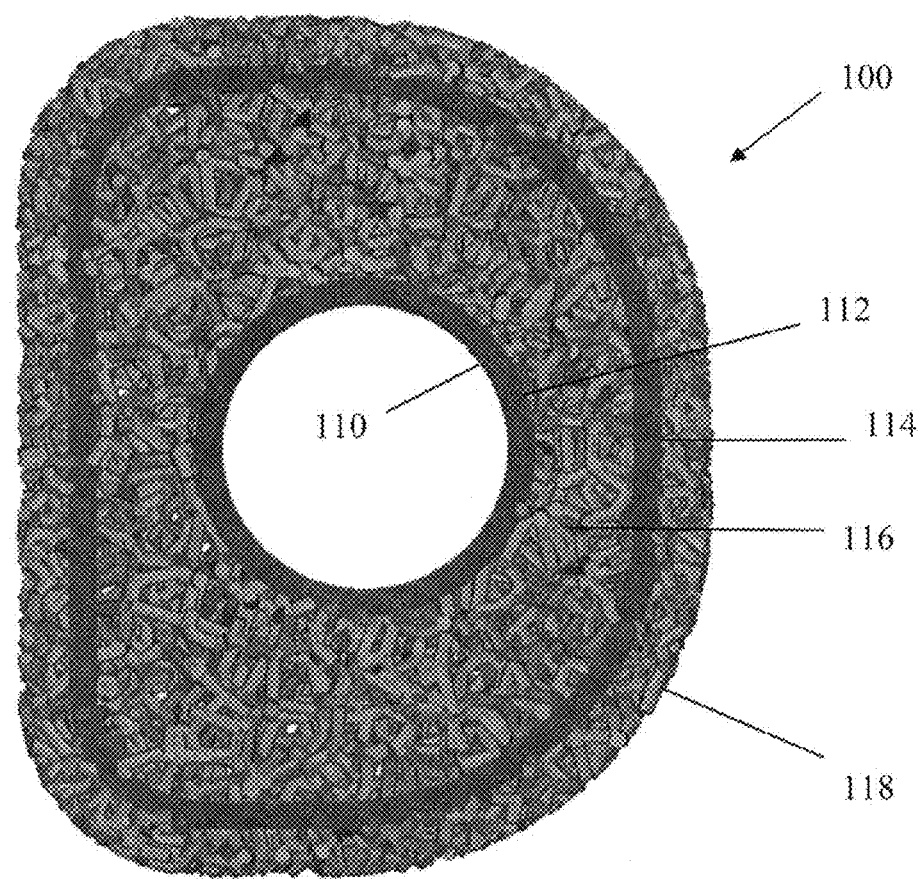
FIG. 2 is a top plan view of an orthopedic implant in accordance with a preferred embodiment of the present invention.
Figure 3:
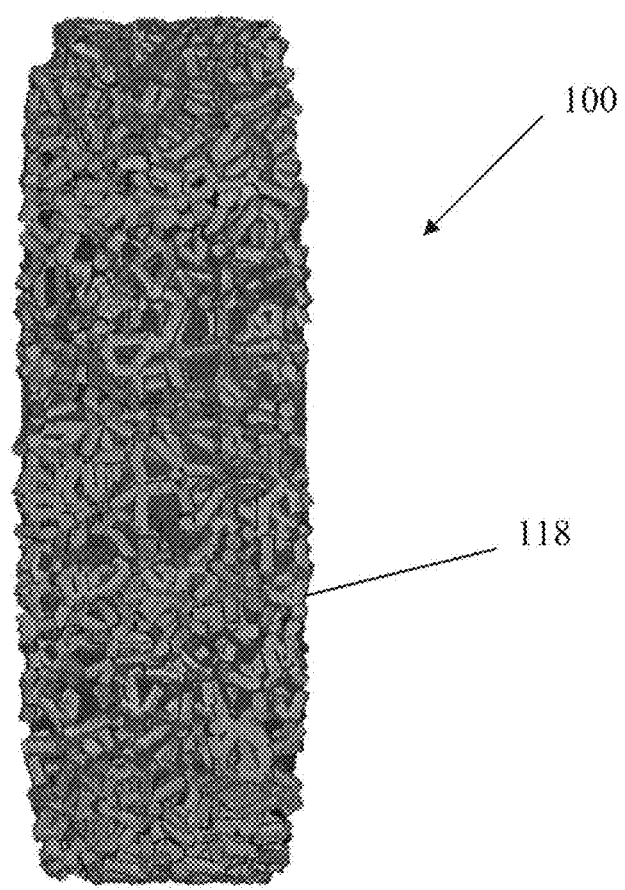
FIG. 3 is a rear side elevation view of the orthopedic implant of FIG. 2.
Figure 4:
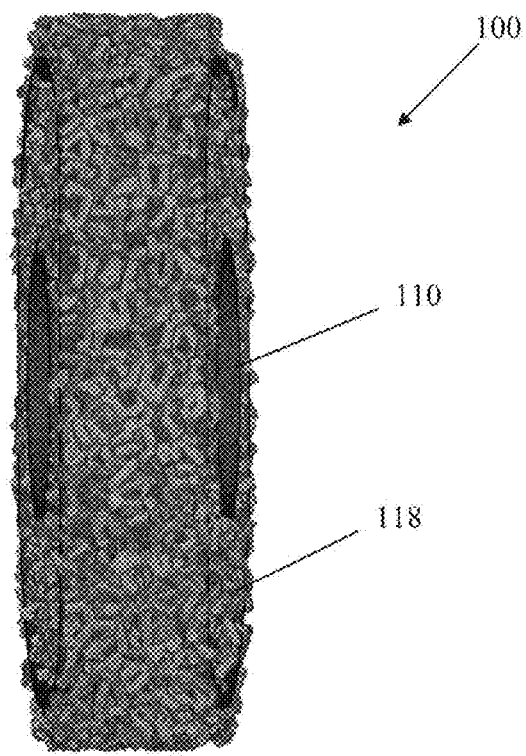
FIG. 4 is a front side elevation view of the orthopedic implant of FIG. 2.
Figure 5:
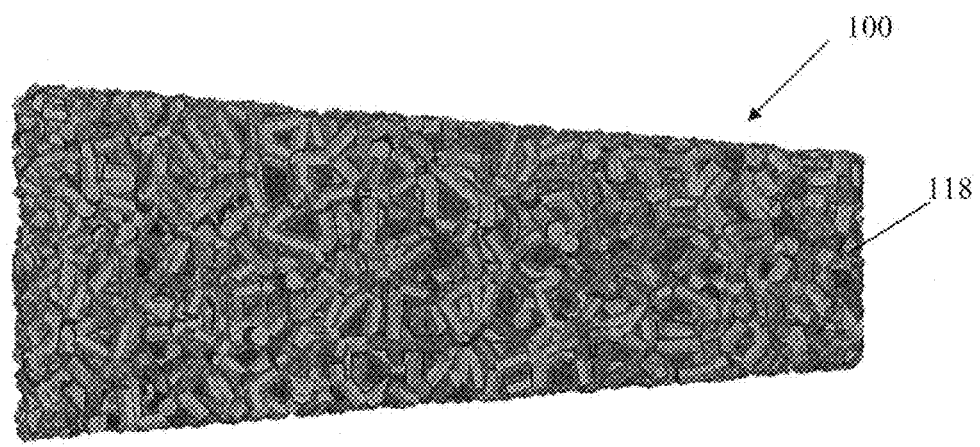
FIG. 5 is a side elevation view of the orthopedic implant of FIG. 2.

Referring to FIGS. 2-5, the wedge implant can be e.g., a metatarsal wedge 100 having a cross-sectional profile that is D-shaped. The metatarsal wedge 100 includes an aperture 110 extending through the wedge at about a central portion thereof. The metatarsal wedge includes a first circumferential solid portion 112 adjacent the aperture 110 and a second circumferential solid portion 114 spaced from the first circumferential solid portion 112. Further, the metatarsal wedge includes a first porous portion 116 between the first and second circumferential solid portions and a second porous portion 118 circumscribing the second circumferential solid portion 114. The various porous and solid portions of the metatarsal wedge 100 are preferably positioned as shown in FIG. 2, such that the porous and solid portions are in a layered fashion. The metatarsal wedge 100 is also configured as a wedge having a sloped edge, as best shown in FIGS. 4 and 5. The aperture on 110 is sized and shaped for receiving a biologic and/or a fixation device, such as a screw or pin.

The solid portions 112 and 114 provide support for higher stressed areas while the porous portions 116 and 118 support bone ingrowth and involucrum. More preferably, the region of the first porous portion 114 proximal to or adjacent the aperture and/or the first solid portion 112 is configured to have a higher density of porous structures compared to the region of the first porous portion 114 distal to the aperture and/or the first solid portion 112. The region of higher density porous structures is to accommodate higher stresses imposed on the implant at or adjacent the aperture 110.

Preferably, the metatarsal wedge 100 as a sized approximately 12×15 mm with a slope or correction angle from about 1 to 20 degrees. However, the overall dimensions can be more or less than the foregoing and modified based upon the particular needs of a patient. The metatarsal wedge 100 can also be used for other osteotomy applications.

Figure 6:
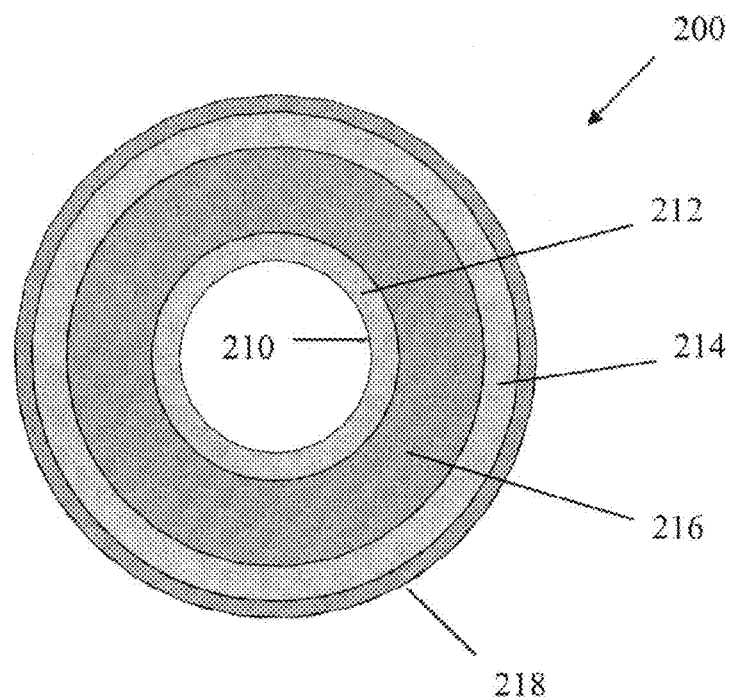
FIG. 6 is a top plan view of an orthopedic implant in accordance with another preferred embodiment of the present invention.

Referring to FIG. 6, the wedge implant can be e.g., a metatarsal/phalange block 200 having a cross-sectional profile that is disc-shaped or donut-shaped. The metatarsal/phalange block 200 can be used for joining the first metatarsal and first phalange joint and similar to the metatarsal wedge 100 includes a first circumferential solid portion 212, a second circumferential solid portion 214 spaced from the first circumferential solid portion 212, a first porous portion 216 between the first and second circumferential solid portions, and a second porous portion 218 circumscribing the second circumferential solid portion 214. Preferably, the metatarsal/phalange block 200 is configured to have a diameter of about 16 mm to 21 mm and a thickness ranging from about 5 mm to 12 mm, but such dimensions can be more or less or modified depending upon a particular patients need. The metatarsal/phalange block 200 may optionally be configured to include an aperture 210 for receiving a biologic and/or a fixation device.

Figure 7:
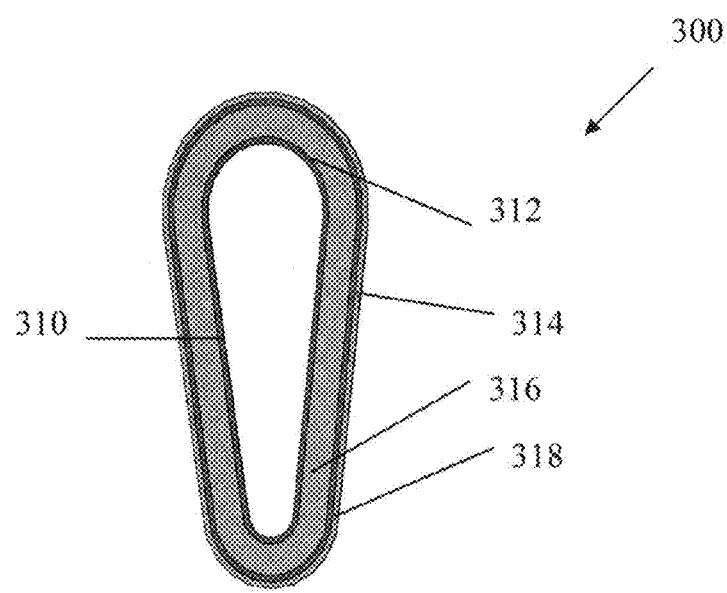
FIG. 7 is a top plan view of an orthopedic implant in accordance with yet another preferred embodiment of the present invention.

Referring to FIG. 7, the wedge implant can be e.g., a metatarsal/cuneiform block 300 having a cross-sectional profile that is tear drop-shaped. The metatarsal/cuneiform block 300 can be used for joining the first metatarsal and medial cuneiform joint and similar to the metatarsal wedge 100 includes a first circumferential solid portion 312, a second circumferential solid portion 314 spaced from the first circumferential solid portion 312, a first porous portion 316 between the first and second circumferential solid portions, and a second porous portion 318 circumscribing the second circumferential solid portion 314. Preferably, the metatarsal/cuneiform block 300 is configured to have dimensions of about 10-15 mm by 15-25 mm and a thickness ranging from about 3 mm to 10 mm, but such dimensions can be more or less or modified depending upon a particular patients need. The metatarsal/cuneiform block 300 may optionally be configured to include an aperture 310 for receiving a biologic and/or a fixation device.

Figure 8:
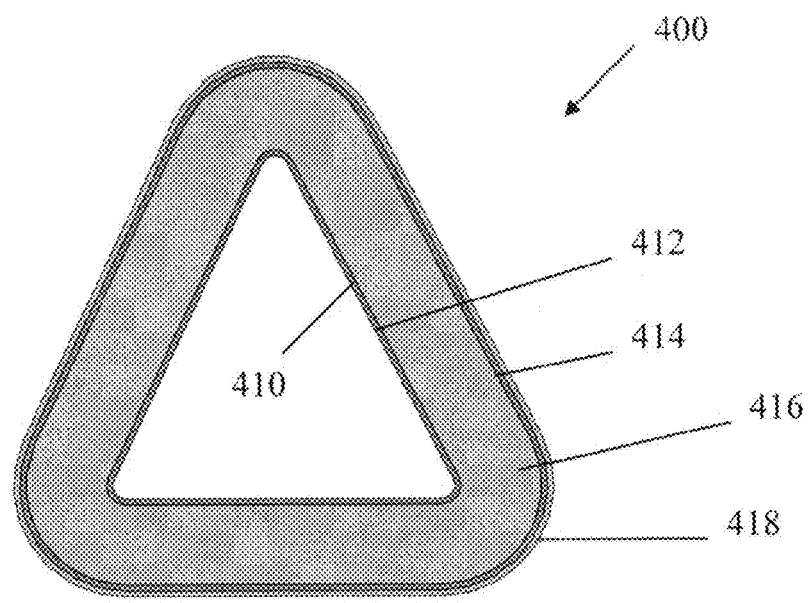
FIG. 8 is a top plan view of an orthopedic implant in accordance with another preferred embodiment of the present invention.
Figure 9:
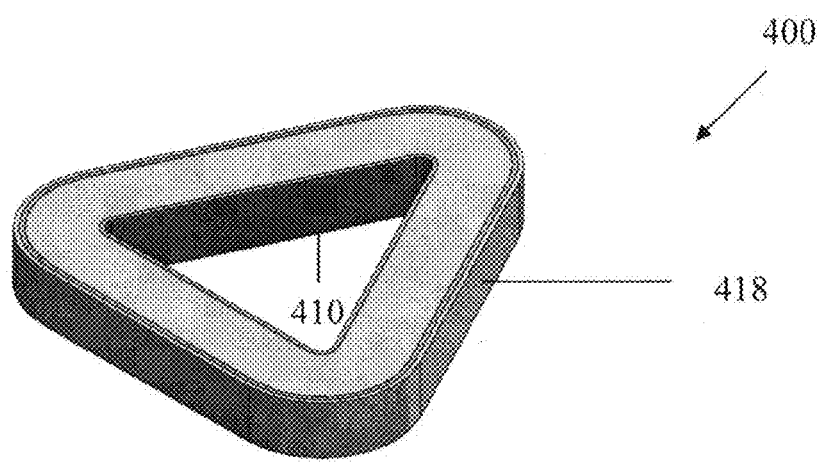
FIG. 9 is a perspective view of the orthopedic implant of FIG. 8.
Figure 10:
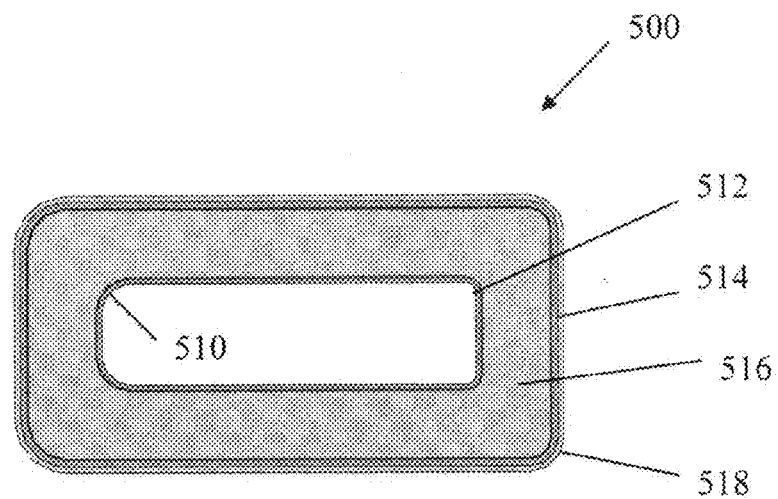
FIG. 10 is a top plan view of an orthopedic implant in accordance with yet another preferred embodiment of the present invention.
Figure 11:
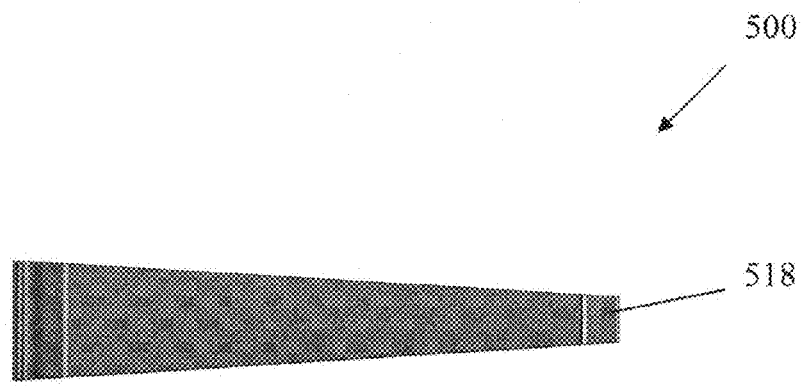
FIG. 11 is a side elevation view of the orthopedic implant of FIG. 10.
Figure 12:
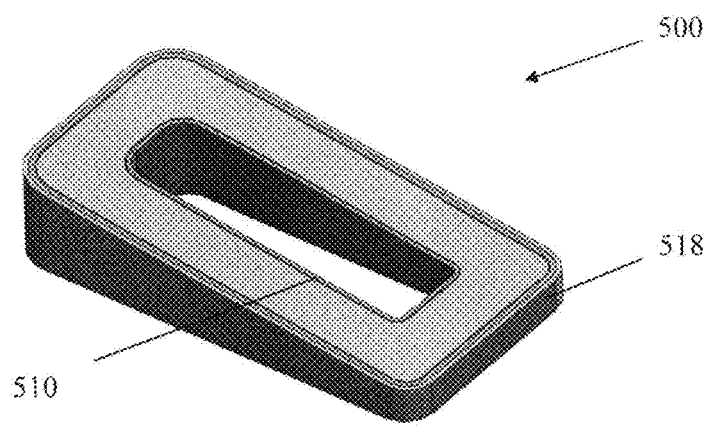
FIG. 12 is a perspective view of the orthopedic implant of FIG. 10.
Figure 13:
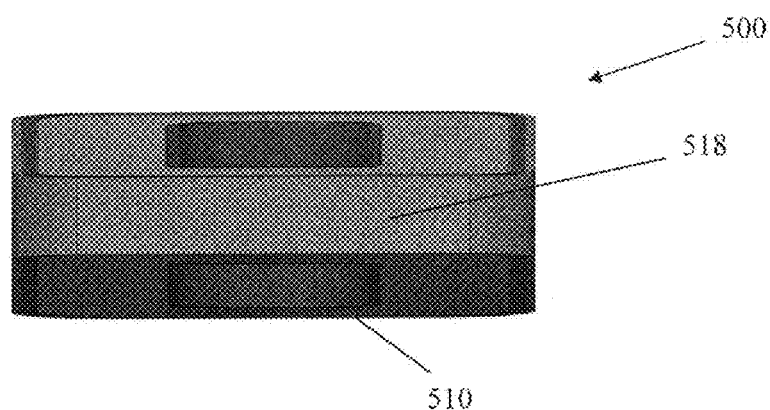
FIG. 13 is a front elevation view of the orthopedic implant of FIG. 10.
Figure 14:
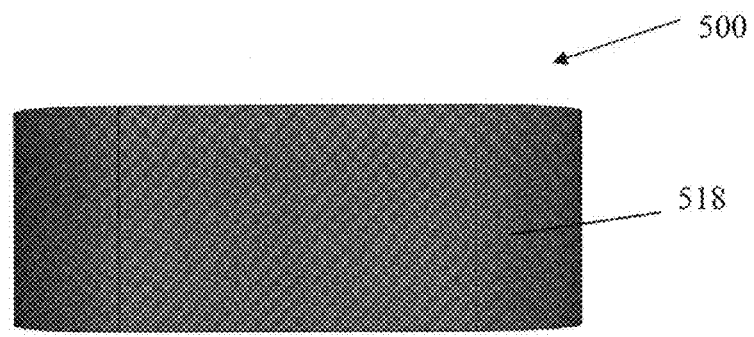
FIG. 14 is a rear elevation view of the orthopedic implant of FIG. 10.

Referring to FIGS. 8 and 9, the wedge implant can be e.g., a calcaneal-cuboid block 400 having a cross-sectional profile that is triangular-shaped. The calcaneal-cuboid block 400 can be used for joining the calcaneal and the cuboid joint and similar to the metatarsal wedge 100 to the metatarsal wedge 100 includes a first circumferential solid portion 412, a second circumferential solid portion 414 spaced from the first circumferential solid portion 412, a first porous portion 416 between the first and second circumferential solid portions, and a second porous portion 418 circumscribing the second circumferential solid portion 414. Preferably, the calcaneal-cuboid block 400 is configured to have a thickness of about 3-20 mm and a size of approximately 20-30 mm and 10-20 mm, but such dimensions can be more or less or modified depending upon a particular patients need. The calcaneal-cuboid block 400 may optionally be configured to include an aperture 410 for receiving a biologic and/or a fixation device.

Referring to FIGS. 10-14, the wedge implant can be e.g., a medial cuneiform opening wedge 500 having a cross-sectional profile that is rectangular-shaped. The medial cuneiform opening wedge 500 can be used with an osteotomy of the medial cuneiform and similar to the metatarsal wedge 100 includes a first circumferential solid portion 512, a second circumferential solid portion 514 spaced from the first circumferential solid portion 512, a first porous portion 516 between the first and second circumferential solid portions, and a second porous portion 518 circumscribing the second circumferential solid portion 514. Preferably, the medial cuneiform opening wedge 500 is configured to have a height of about 25 mm, a plantar width of about 10 mm, a dorsal width of about 14 mm, and a thickness of about 5-12 mm, but such dimensions can be more or less or modified depending upon a particular patients need. The medial cuneiform opening wedge 500 may optionally be configured to include an aperture 510 for receiving a biologic and/or a fixation device.

Figure 15:
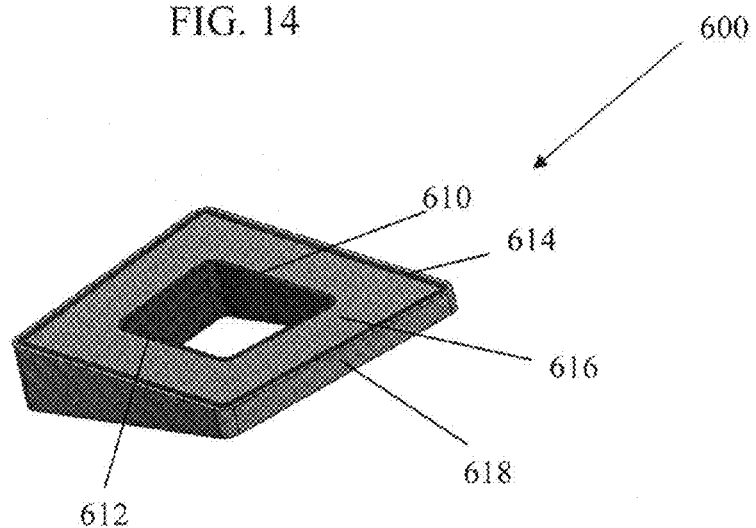
FIG. 15 is a perspective view of an orthopedic implant in accordance with another preferred embodiment of the present invention.
Figure 16:
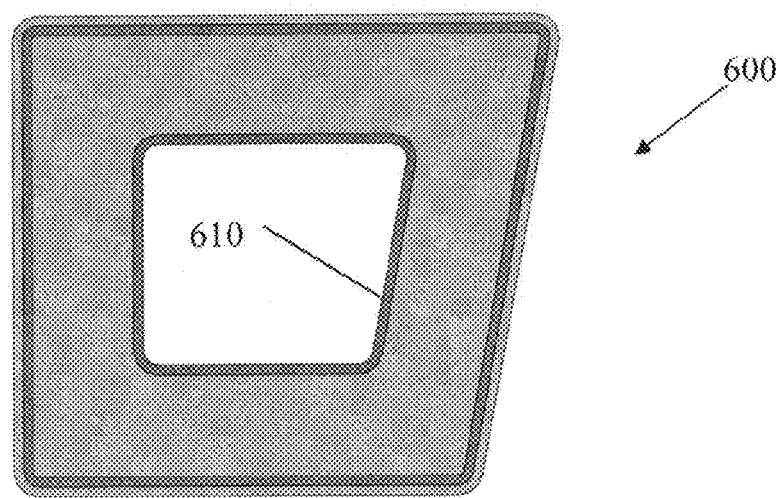
FIG. 16 is a top plan view of the orthopedic implant of FIG. 15.
Figure 17:
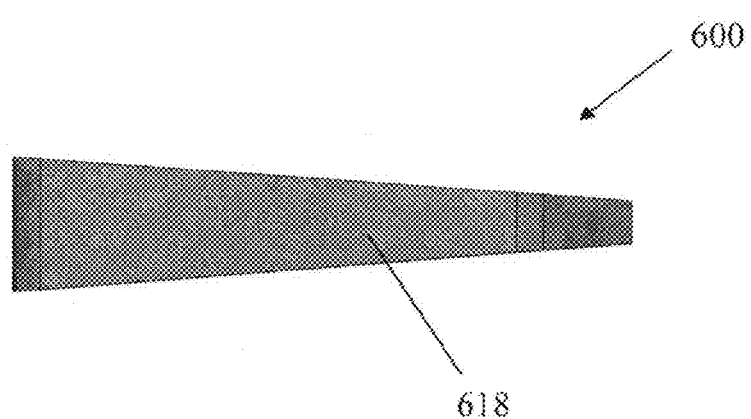
FIG. 17 is a side elevation view of the orthopedic implant of FIG. 15.

Referring to FIGS. 15-17, the wedge implant can be e.g., a calcaneal lengthening/angle correcting wedge 600 having a cross-sectional profile that is trapezoidal-shaped. The calcaneal lengthening/angle correcting wedge 600 can be used with an opening osteotomy of the calcaneous and similar to the metatarsal wedge 100 includes a first circumferential solid portion 612, a second circumferential solid portion 614 spaced from the first circumferential solid portion 612, a first porous portion 616 between the first and second circumferential solid portions, and a second porous portion 618 circumscribing the second circumferential solid portion 614. Preferably, the calcaneal lengthening/angle correcting wedge 600 is configured to have an angular wedge of about 6 mm to 14 mm in thickness, a depth of about 20 mm to 25 mm, and a height of about 20 mm, but such dimensions can be more or less or modified depending upon a particular patients need. The calcaneal lengthening/angle correcting wedge 600 may optionally be configured to include an aperture 610 for receiving a biologic and/or a fixation device.

Figure 18:
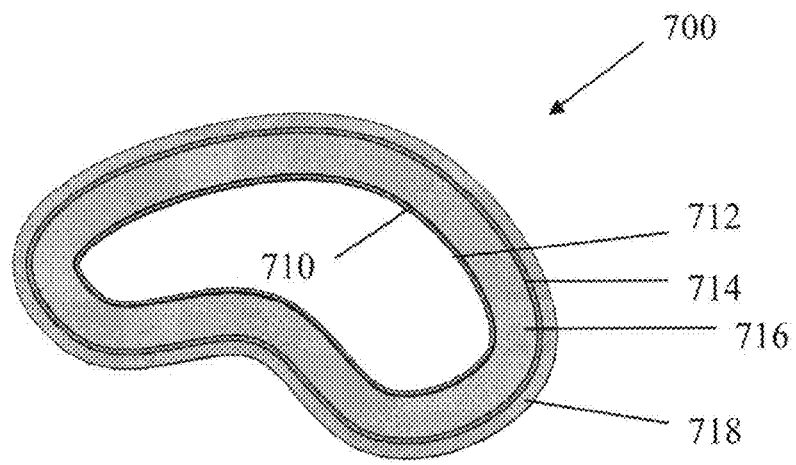
FIG. 18 is a top plan view of an orthopedic implant in accordance with another preferred embodiment of the present invention.

Referring to FIG. 18, the wedge implant can be e.g., a navicular-cuneiform block 700 having a cross-sectional profile that is sickle-shaped or kidney-shaped. The navicular-cuneiform block 700 can be used for joining the navicular and medial cuneform joints and similar to the metatarsal wedge 100 includes a first circumferential solid portion 712, a second circumferential solid portion 714 spaced from the first circumferential solid portion 712, a first porous portion

716 between the first and second circumferential solid portions, and a second porous portion 718 circumscribing the second circumferential solid portion 714. Preferably, the navicular-cuneiform block 700 is configured to have dimensions of about 10-21 mm by 20-32 mm, 0 to 12 degrees of angulation and thickness ranging from about 3-15 mm, but such dimensions can be more or less or modified depending upon a particular patients need. The navicular-cuneiform block 700 may optionally be configured to include an aperture 710 for receiving a biologic and/or a fixation device.

Figure 19:
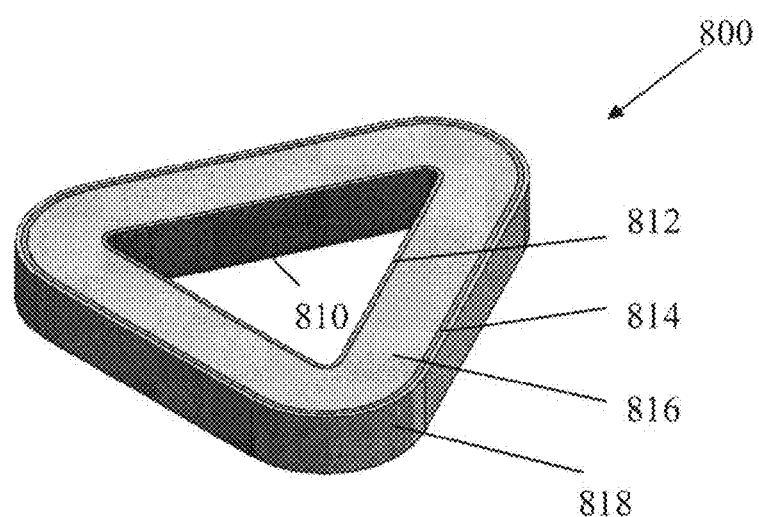
FIG. 19 is a perspective view of an orthopedic implant in accordance with yet another preferred embodiment of the present invention.

Referring to FIG. 19, the wedge implant can be e.g., a wedge block 800 having a cross-sectional profile that is triangular-shaped. The wedge block 800 similar to the metatarsal wedge 100 includes a first circumferential solid portion 812, a second circumferential solid portion 814 spaced from the first circumferential solid portion 812, a first porous portion 816 between the first and second circumferential solid portions, and a second porous portion 818 circumscribing the second circumferential solid portion 814. Preferably, the wedge block 800 is configured to have a thickness of about 3-10 mm and a size of about 20-35 mm by 10-20 mm, but such dimensions can be more or less or modified depending upon a particular patients need. The wedge block 800 may optionally be configured to include an aperture 810 for receiving a biologic and/or a fixation device.

Figure 20:
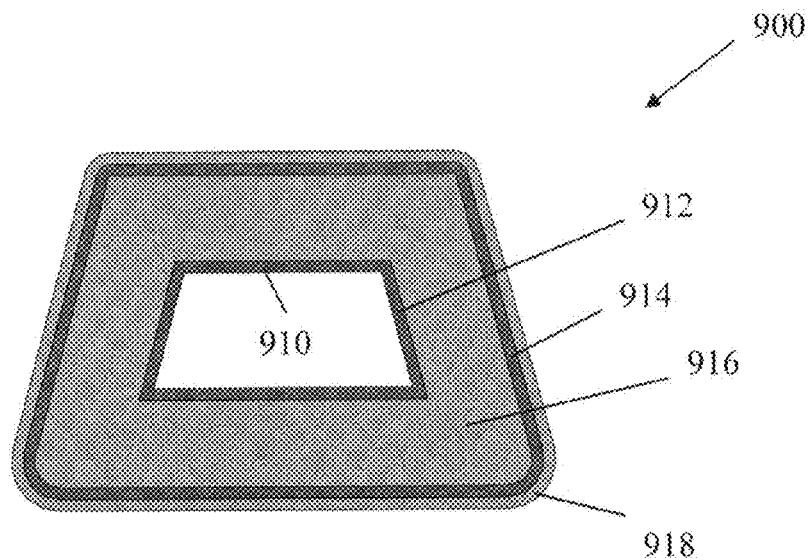
FIG. 20 is a top plan view of an orthopedic implant in accordance with another preferred embodiment of the present invention.
Figure 21:
FIG. 21 is a rear side elevation view of the orthopedic implant of FIG. 20.
Figure 22:
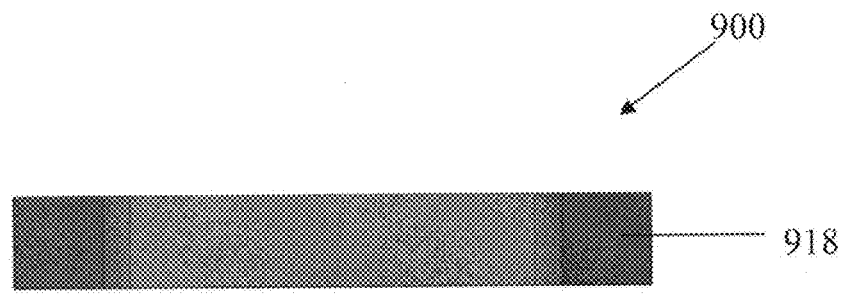
FIG. 22 is a front side elevation view of the orthopedic implant of FIG. 20.
Figure 23:
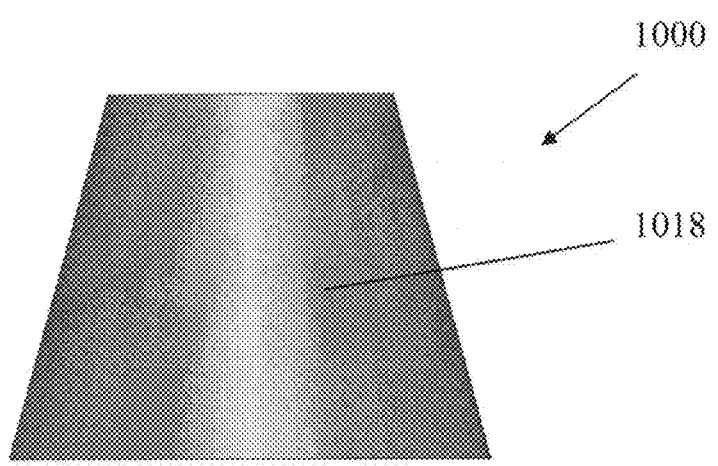
FIG. 23 is a side elevation view of an orthopedic implant in accordance with another preferred embodiment of the present invention.
Figure 24:
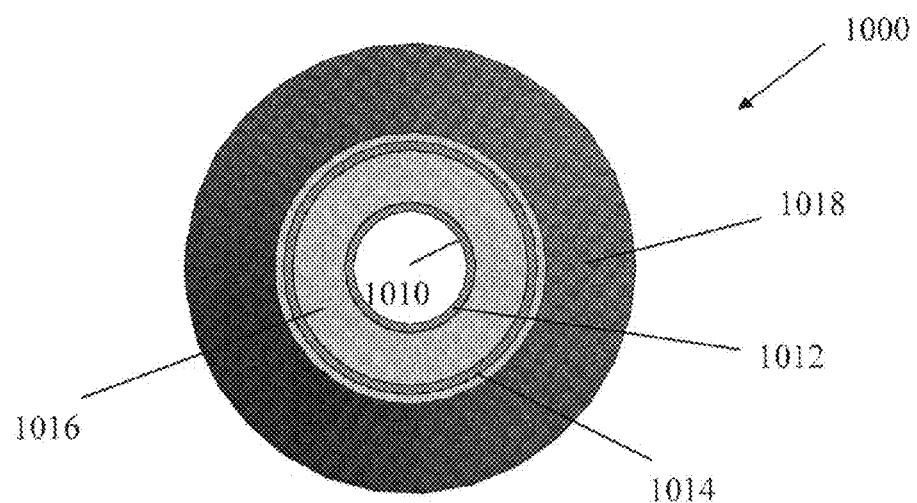
FIG. 24 is a top plan view of the orthopedic implant of FIG. 23.
Figure 25:
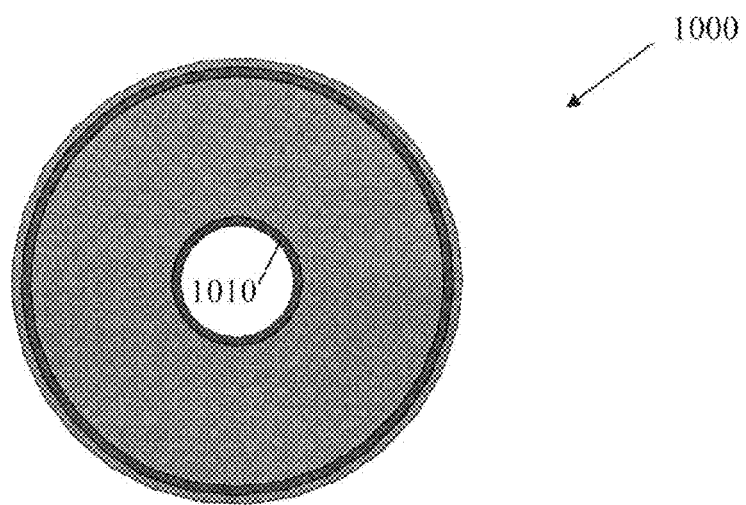
FIG. 25 is a bottom plan view of the orthopedic implant of FIG. 23.
Figure 26:
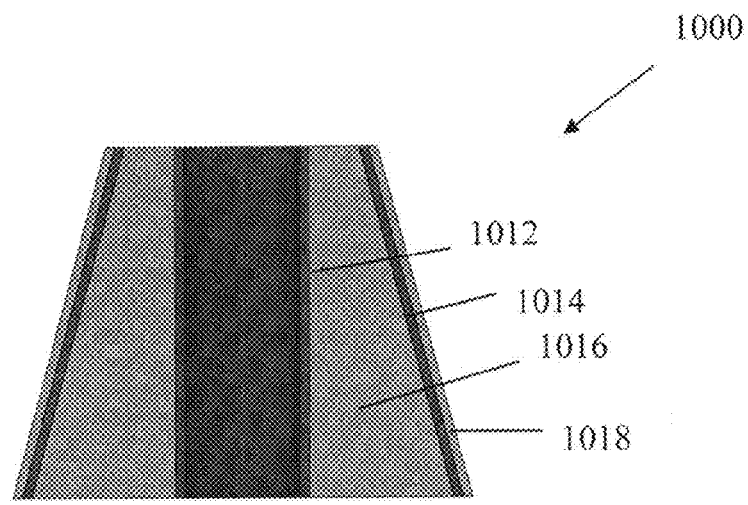
FIG. 26 is a cross-section view of the orthopedic implant of FIG. 23.

Referring to FIGS. 20-22, the wedge implant can be e.g., a wedge block 900 having a cross-sectional profile that is trapezoidal-shaped. The wedge block 900 similar to the metatarsal wedge 100 includes a first circumferential solid portion 912, a second circumferential solid portion 914 spaced from the first circumferential solid portion 912, a first porous portion 916 between the first and second circumferential solid portions, and a second porous portion 918 circumscribing the second circumferential solid portion 914. Preferably, the wedge block 900 is configured to have a height of about 3-15 mm and a size of about 20 mm by 30 mm, but such dimensions can be more or less or modified depending upon a particular patients need. The wedge block 900 may optionally be configured to include an aperture 910 for receiving a biologic and/or a fixation device.

Referring to FIGS. 23-26, the wedge implant can be e.g., an implant 1000 having a cross-sectional profile that is frustum-shaped or of a tapered cylinder design. The implant 1000 similar to the metatarsal wedge 100 includes a first circumferential solid portion 1012, a second circumferential solid portion 1014 spaced from the first circumferential solid portion 1012, a first porous portion 1016 between the first and second circumferential solid portions, and a second porous portion 1018 circumscribing the second circumferential solid portion 1014. Preferably, the implant 1000 is configured to have a diameter of about 20 mm at its proximal end and a diameter of about 25 mm at its distal end, but such dimensions can be more or less or modified depending upon a particular patients need. The implant 1000 may optionally be configured to include an aperture 1010 for receiving a biologic and/or a fixation device.

Figure 27:
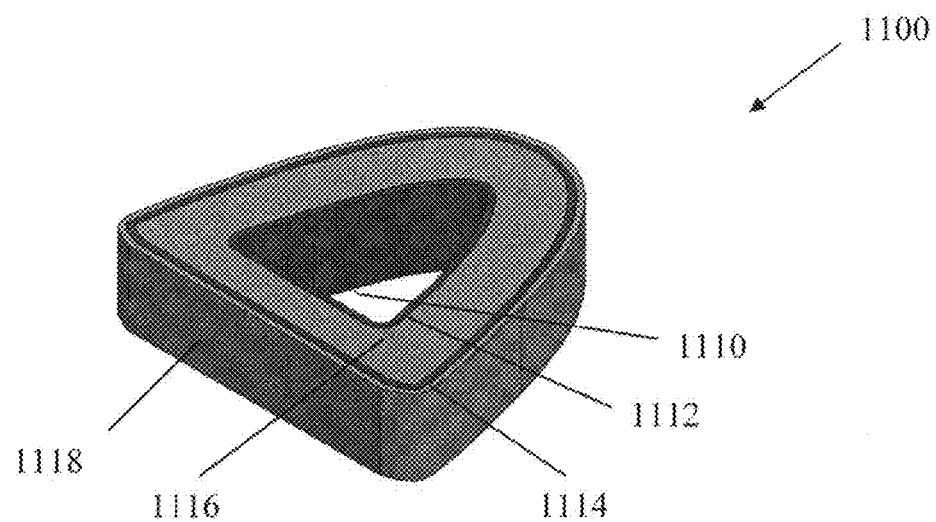
FIG. 27 is a perspective view of an orthopedic implant in accordance with yet another preferred embodiment of the present invention.

Referring to FIG. 27, the wedge implant can be e.g., an implant 1100 having a cross-sectional profile that is D-shaped e.g., like the capital letter D. The implant 1100 similar to the metatarsal wedge 100 includes a first circumferential solid portion 1112, a second circumferential solid portion 1114 spaced from the first circumferential solid portion 1112, a first porous portion 1116 between the first and second circumferential solid portions, and a second porous portion 1118 circumscribing the second circumferential solid portion 1114. Preferably, the implant 1100 is configured to have a thickness of about 3-15 mm and a size of about 20-25 mm, but such dimensions can be more or less or modified depending upon a particular patients need. The implant 1100 may optionally be configured to include an aperture 1110 for receiving a biologic and/or a fixation device.

Figure 28:
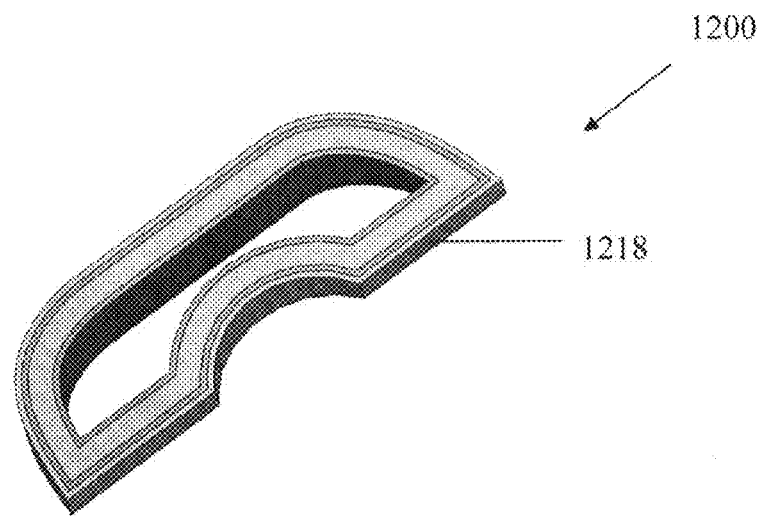
FIG. 28 is a perspective view of an orthopedic implant in accordance with another preferred embodiment of the present invention.
Figure 29:
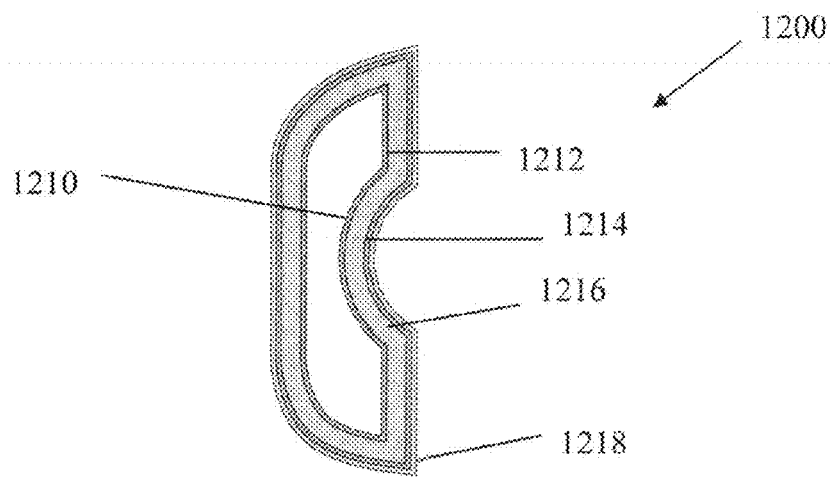
FIG. 29 is a top plan view of the orthopedic implant of FIG. 28.
Figure 30:
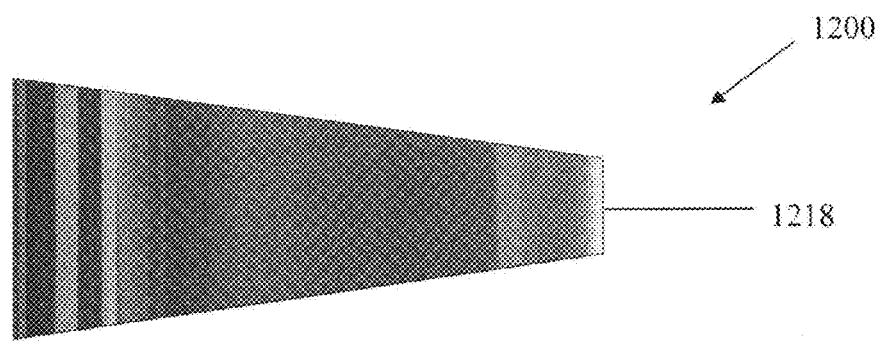
FIG. 30 is a side elevation view of the orthopedic implant of FIG. 28.

Referring to FIGS. 28-30, the wedge implant can be e.g., a femur/tibial osteotomy opening wedge 1200 having a cross-sectional profile that best shown in FIG. 29. The implant femur/tibial osteotomy opening wedge 1200 can be used for correcting the anatomical axis at the distal femur, proximal and/or distal tibia. And similar to the metatarsal wedge 100 includes a first circumferential solid portion 1212, a second circumferential solid portion 1214 spaced from the first circumferential solid portion 1212, a first porous portion 1216 between the first and second circumferential solid portions, and a second porous portion 1218 circumscribing the second circumferential solid portion 1214. Preferably, the femur/tibial osteotomy opening wedge 1200 is configured to have a thickness that varies from about 3 mm to 18 mm and a size of about 20-35 mm long and a depth of about 10-20 mm, but such dimensions can be more or less or modified depending upon a particular patients need. The femur/tibial osteotomy opening wedge 1100 may optionally be configured to include an aperture 1110 for receiving a biologic and/or a fixation device.

Figure 31:
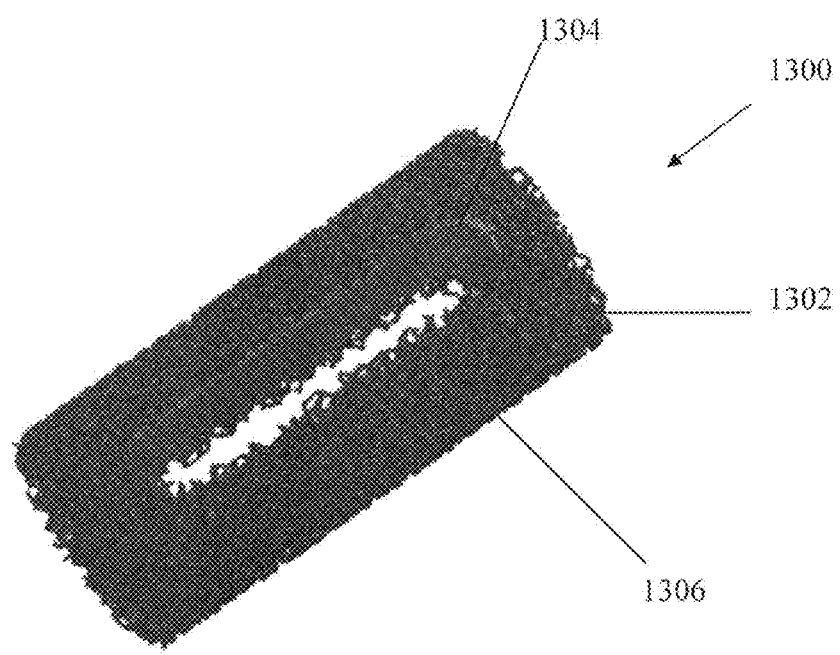
FIG. 31 is a perspective view of an orthopedic implant in accordance with yet another preferred embodiment of the present invention.
Figure 32:
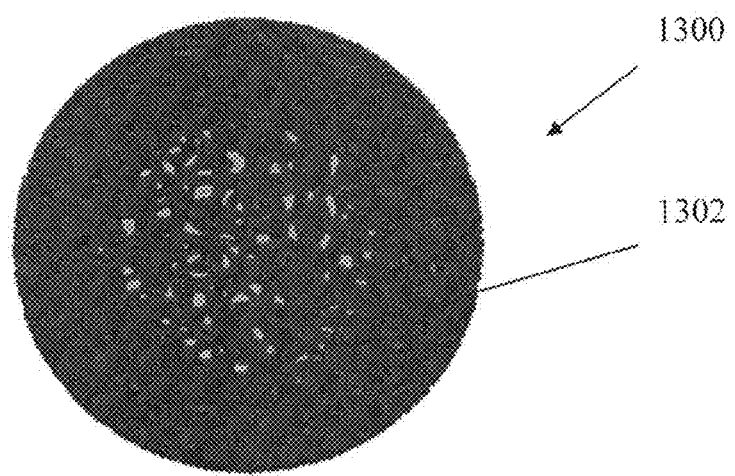
FIG. 32 is a end side elevation view of the orthopedic implant of FIG. 31.
Figure 33:
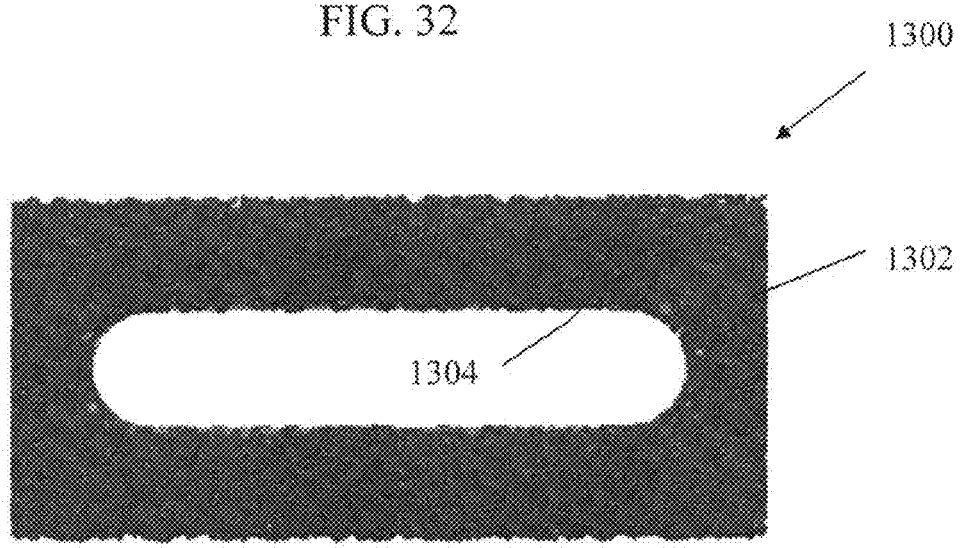
FIG. 33 is a top plan view of the orthopedic implant of FIG. 31.

Referring to FIGS. 31-33, the implant 1300 can comprise a cylindrical solid body 1302 and a porous coating 1306 surrounding the cylindrical solid body. For example, the implant can be a talar navicular implant, an ankle block or an ankle subtalar block, configured e.g., as shown. The implant can be used, for example, to join the talar and navicular joint, to join the tabial and talar joint, or to join the talar and calcaneous joint. The implant 1300 can further include an aperture 1304 extending through the solid body. The aperture 1304 extends through the solid body substantially transverse to a longitudinal axis of the cylindrical solid body. The implant 1300 may optionally be configured to include one or more additional thru holes for receiving a biologic and/or a fixation device or have the biologic and/or fixation device received within the aperture 1304. Preferably, the implant is configured to have a diameter of about 5-14 mm and more preferably about 5-10 mm or 10-14 mm, and a longitudinal length of about 10-30 mm and more preferably about 10-20 mm or 25-30 mm, but such dimensions can be more or less or modified depending upon a particular patients need.

Figure 34:
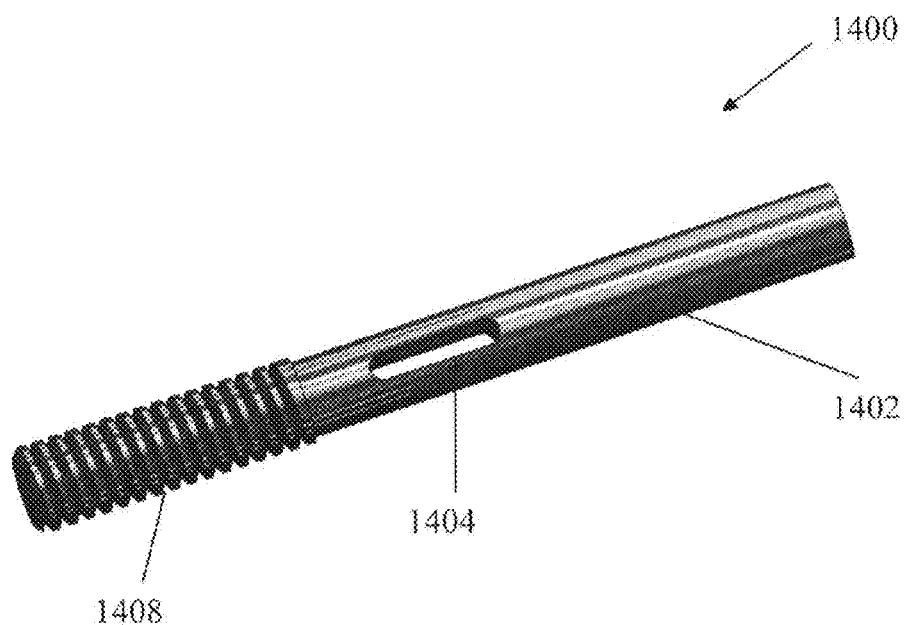
FIG. 34 is a perspective view of an orthopedic implant in accordance with another preferred embodiment of the present invention.
Figure 35:
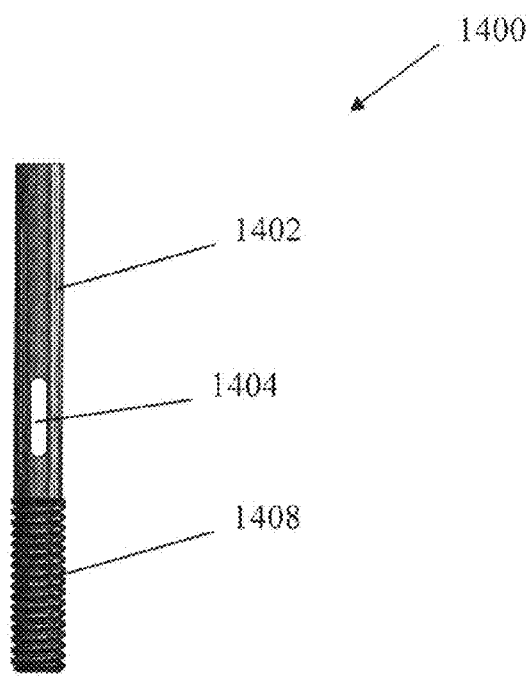
FIG. 35 is a side elevation view of the orthopedic implant of FIG. 34.

Referring to FIGS. 34 and 35, the ankle rod 1400 is a substantially cylindrical rod configured e.g., as shown. The ankle rod includes a substantially cylindrical solid body 1402, a porous coating 1406 surrounding the cylindrical solid body and a fastener 1408 at one end of the ankle rod implant. The fastener is preferably configured as threads. The ankle rod can optionally include an aperture 1404 extending through the solid body. The aperture 1404 extends through the solid body substantially transverse to a longitudinal axis of the cylindrical solid body. In operation, the fastener 1408 is implanted into the calcaneous and talar regions such that the remainder of the rod extends into the intermedullary canal of the distal tibia. Preferably, the ankle rod is configured to have a diameter of about 10-14 mm and a longitudinal length of about 150 mm, but such dimensions can be more or less or modified depending upon a particular patients need.

Figure 36:
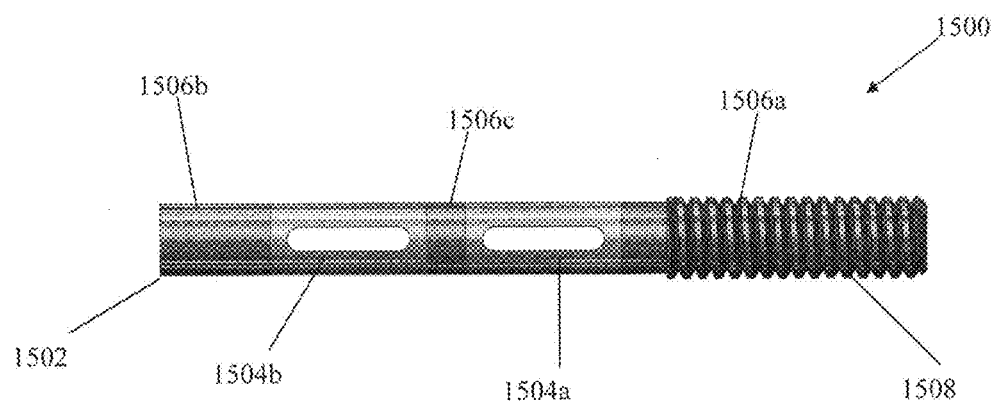
FIG. 36 is a top plan view of an orthopedic implant in accordance with yet another preferred embodiment of the present invention.
Figure 37:
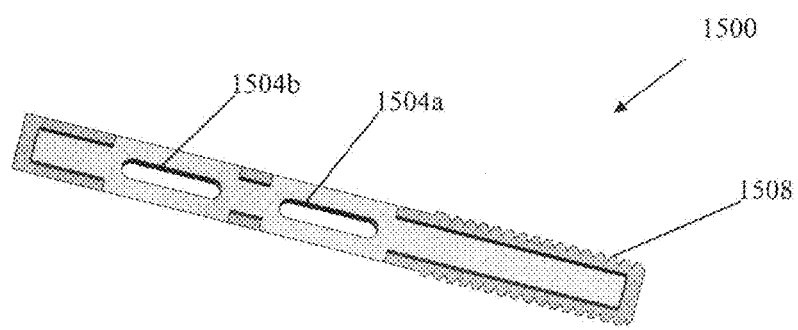
FIG. 37 is a cross-sectional perspective view of the orthopedic implant of FIG. 36.

Referring to FIGS. 36 and 37, the rod implant 1500 can be e.g., a talar navicular cuneiform rod that is a substantially cylindrical rod configured e.g., as shown. The rod implant includes a substantially cylindrical solid body 1502 and a fastener 1508 at a first end of the rod implant. The fastener is preferably configured as threads. The rod implant further includes a first porous coating region 1506*a* covering the fastener, a second porous coating region 1506*b* covering a second end of the rod implant, and a third porous coating region 1506*c* covering a portion of the cylindrical solid body spaced from the first and second coating regions. The porous coating can be intermittent throughout the length of the implant, so as to have regions where the implant does not include a porous coating. The rod implant 1500 can optionally include an aperture 1504*a* and preferably two spaced apart apertures i.e., first 1504*a* and second 1504*b* apertures extending through the solid body. The apertures 1504*a* and 1504*b* extend through the solid body substantially transverse to a longitudinal axis of the cylindrical solid body. The rod implant 1500 can be used to join the talar and navicular joint, as well as the navicular and medial cuneiform joint. Preferably, the rod implant is configured to have a diameter of about 5-10 mm and a longitudinal length of about 70-75 mm, but such dimensions can be more or less or modified depending upon a particular patients need.

In accordance with another preferred embodiment, the present invention provides an orthopedic implant that includes a first solid portion, a second solid portion spaced from and circumscribing the first solid portion. Further, the implant includes a first porous portion between the first and second solid portions and a second porous portion circumscribing the second solid portion. Furthermore, the implant is formed completely by additive manufacturing based on a 3D model of the implant.

The 3D model of the implant has a defined surface area percentage for each of the first solid portion, the second solid portion, the first porous portion, and the second porous portion. The surface area percentages of the 3D model is modified based upon a position the implant is to be implanted in bone i.e., a determined position the implant is to be implanted. The implant can be configured as or configured to have a cross-section profile similar to any of the above-described embodiments.

It will be appreciated by those skilled in the art that changes could be made to the embodiments described above without departing from the broad inventive concept thereof. It is to be understood, therefore, that this invention is not limited to the particular embodiments disclosed, but it is intended to cover modifications within the spirit and scope of the present invention as defined by the appended claims.

I claim:

1. A method of manufacturing an orthopedic implant comprising:
    creating a 3D model of a part having a solid portion and a porous portion, and an aperture extending through the part;
    selectively adjusting the degree of porosity of the porous portion adjacent the aperture to be higher than the degree of porosity of the porous portion distal to the aperture; and
    additively manufacturing the entire orthopedic implant based on the 3D model of the part.

2. The method of claim 1, wherein the step of additively manufacturing includes direct metal laser sintering the entire orthopedic implant, selective laser sintering the entire orthopedic implant or electron beam melting the entire orthopedic implant.

3. The method of claim 1, wherein the step of selectively adjusting the physical properties of the porous portion includes continuously varying the degree of porosity of the porous portion.

4. The method of claim 1, wherein the step of creating the 3D model includes creating the part to include a first solid portion, a second solid portion spaced from and circumscribing the first solid portion, a first porous portion between the first and second solid portions, and a second porous portion circumscribing the second solid portion.

5. The method of claim 4, further comprising modifying a surface area percentage of the first solid portion, the second solid portion, the first porous portion, and the second porous portion of the 3D model based on an intended type of bone the orthopedic implant is intended to be implanted in.

6. The method of claim 1, wherein the step of creating the 3D model includes creating the part to include a first porous portion and a second porous portion having a degree of porosity that differs from a degree of porosity of the first porous portion.

7. A method of manufacturing an orthopedic implant comprising:
    creating a 3D model of a part having a first solid portion, a second solid portion spaced from and circumscribing the first solid portion, a first porous portion between the first and second solid portions, and a second porous portion circumscribing the second solid portion, and an aperture extending through the part;
    selectively adjusting the degree of porosity of the first or second porous portions of the 3D model adjacent the aperture to be higher than the degree of porosity distal to the aperture; and
    additively manufacturing the entire orthopedic implant based on the 3D model of the part.

8. The method of claim 7, further comprising modifying a surface area percentage of the first solid portion, the second solid portion, the first porous portion, and the second porous portion of the 3D model based on an intended type of bone the orthopedic implant is intended to be in contact with.

9. The method of claim 8, wherein the type of bone is cancellous bone or cortical bone.

10. The method of claim 7, wherein the step of creating the 3D model includes creating the part to include the first porous portion and the second porous portion having a degree of porosity that differs from the degree of porosity of the first porous portion.

11. A method of manufacturing an orthopedic implant comprising:
    creating a 3D model of a part having an aperture extending through the part and a first solid portion, a second solid portion spaced from and circumscribing the first solid portion, a first porous portion between the first and second solid portions, and a second porous portion circumscribing the second solid portion;
    selectively adjusting the degree of porosity adjacent to the aperture to differ from the degree of porosity distal to the aperture; and
    additively manufacturing the entire orthopedic implant based on the 3D model of the part.

12. The method of claim 11, wherein the step of selectively adjusting the porosity includes varying the degree of porosity across the first or second porous portions.

13. The method of claim 11, further comprising modifying a surface area percentage of the first solid portion, the second solid portion, the first porous portion, and the second porous portion of the 3D model based on the type of bone the implant is intended to contact with.

14. The method of claim 11, wherein the step of creating the 3D model includes creating the part to include the first porous portion and the second porous portion having a degree of porosity that differs from the degree of porosity of the first porous portion.

\* \* \* \* \*